US011129951B2

(12) United States Patent
Whitman et al.

(10) Patent No.: US 11,129,951 B2
(45) Date of Patent: *Sep. 28, 2021

(54) MEDICAL VAPORIZER

(71) Applicant: General Electric Company, Schenectady, NY (US)

(72) Inventors: Shawn Thomas Whitman, Cambridge, WI (US); Michael Eric Jones, Sun Prairie, WI (US); Robert Q. Tham, Madison, WI (US)

(73) Assignee: General Electric Company, Schenectady, NY (US)

( * ) Notice: Subject to any disclaimer, the term of this patent is extended or adjusted under 35 U.S.C. 154(b) by 947 days.

This patent is subject to a terminal disclaimer.

(21) Appl. No.: 15/397,296

(22) Filed: Jan. 3, 2017

(65) Prior Publication Data

US 2017/0113010 A1  Apr. 27, 2017

Related U.S. Application Data

(63) Continuation of application No. 14/197,915, filed on Mar. 5, 2014, now Pat. No. 9,566,404.

(51) Int. Cl.
*A61M 16/01* (2006.01)
*A61B 5/055* (2006.01)
(Continued)

(52) U.S. Cl.
CPC ............. *A61M 16/01* (2013.01); *A61B 5/055* (2013.01); *A61M 11/00* (2013.01);
(Continued)

(58) Field of Classification Search
CPC .. A61M 11/041; A61M 11/042; A61M 16/18; A61M 2016/1035;
(Continued)

(56) References Cited

U.S. PATENT DOCUMENTS 4,833,892 A * 5/1989 Wassibauer ........... A23L 3/3418
62/216
8,867,031 B2  10/2014 Jones et al.
(Continued)

FOREIGN PATENT DOCUMENTS

JP  2012-217500 A  11/2012
WO  2013/147623 A1  10/2013

OTHER PUBLICATIONS

First Office Action and Search issued in connection with corresponding CN Application No. 201580012063.1 dated Oct. 31, 2018, 16 pages.

*Primary Examiner* — Nathan R Price
*Assistant Examiner* — Justin L Zamory
(74) *Attorney, Agent, or Firm* — Andrus Intellectual Property Law, LLP (57) ABSTRACT

A medical vaporizer includes a liquid drug reservoir configured to receive and hold a liquid drug. A low power graphical display is configured to intermittently receive power. The low power graphical display is operable to visually present information and maintain the visual presentation of information in the absence of power. A controller is configured to intermittently receive power and upon receiving power the controller operates to determine a status of a medical vaporizer. The controller operates the low power graphical display to present the status of the medical vaporizer as visually presented information.

16 Claims, 6 Drawing Sheets

(51) Int. Cl.
 *A61M 11/00* (2006.01)
 *A61M 16/00* (2006.01)
 *A61M 16/18* (2006.01)
 *A61M 11/04* (2006.01)

(52) U.S. Cl.
 CPC ......... *A61M 11/041* (2013.01); *A61M 11/042* (2014.02); *A61M 16/0051* (2013.01); *A61M 16/021* (2017.08); *A61M 16/18* (2013.01); *A61M 2202/048* (2013.01); *A61M 2205/3379* (2013.01); *A61M 2205/3386* (2013.01); *A61M 2205/3569* (2013.01); *A61M 2205/3592* (2013.01); *A61M 2205/502* (2013.01); *A61M 2205/60* (2013.01); *A61M 2205/8206* (2013.01); *A61M 2205/8243* (2013.01); *A61M 2205/8262* (2013.01)

(58) Field of Classification Search
 CPC .. A61M 2205/3569; A61M 2205/3592; A61M 16/021; A61M 16/01; A61M 2205/3379; A61M 2205/3382; A61M 2205/3386; A61M 2202/048; A61B 5/055

USPC ............. 128/202.22, 203.12, 203.14, 203.27
 See application file for complete search history.

(56) References Cited

U.S. PATENT DOCUMENTS

| | | | |
|---|---|---|---|
| 2004/0070620 A1* | 4/2004 | Fujisawa | H04N 21/4622 715/764 |
| 2007/0247422 A1 | 10/2007 | Vertegaal et al. | |
| 2011/0036346 A1 | 2/2011 | Cohen et al. | |
| 2011/0155131 A1 | 6/2011 | Bottom | |
| 2011/0227237 A1* | 9/2011 | Hertz | A61M 16/145 261/129 |
| 2013/0147623 A1 | 6/2013 | Somasundaram et al. | |
| 2013/0255676 A1 | 10/2013 | Kuehl et al. | |
| 2013/0276780 A1* | 10/2013 | Tobia | A61M 16/0051 128/202.22 |
| 2015/0048530 A1* | 2/2015 | Cheung | A61M 16/16 261/129 |

\* cited by examiner

MEDICAL VAPORIZER

CROSS REFERENCE TO RELATED APPLICATION

This application is continuation of U.S. application Ser. No. 14/197,915, filed Mar. 5, 2014, which application was published on Sep. 10, 2015, as U.S. Publication No. US20150250961, which application is incorporated herein by reference in its entirety.

BACKGROUND

The present disclosure is related to the field of anesthesia delivery. More specifically, the present disclosure is related to medical vaporizers.

Medical vaporizers are devices that hold a volume of liquid drug exemplarily for use with an anesthesia delivery machine. The vaporizer operates to convert the liquid drug to a gaseous state. The delivery of the gaseous drug to the patient is facilitated by the interaction of the anesthesia delivery machine with the vaporizer.

Modern electronic vaporizers may not be considered compatible for use with a magnetic resonance imaging (MRI) machine if the vaporizer has an electronic LED or LCD display, due to the strong magnetic field associated with the MRI machine. Some previous solutions have relied upon electromagnetic shielding over the electronic LCD or LED display. Such electromagnetic shielding reduces the brightness and impairs visibility of the display. Additionally, if it is desired that the electronic display of the vaporizer be operational when the vaporizer is not connected to an anesthesia delivery machine, the vaporizer must also include a battery. However, this introduces further disadvantages, including battery charging, monitoring, replacement, and disposal.

BRIEF DISCLOSURE

An exemplary embodiment of a medical vaporizer includes a liquid drug reservoir configured to receive and hold a liquid drug. A low power graphical display is configured to intermittently receive power. The low power graphical display is operable to visually present information and maintain the visual presentation of information in the absence of power. A controller is configured to intermittently receive power. Upon receiving power, the controller operates to determine a status of the medical vaporizer. The controller operates the low power graphical display to present the status of the medical vaporizer as visually presented information.

In an exemplary embodiment of a method of operation of a medical vaporizer, the medical vaporizer includes a liquid drug reservoir configured to receive and hold a liquid drug, a low power graphical display, and a controller. The medical vaporizer receives power from an external power source external to the medical vaporizer. The controller determines a status of the medical vaporizer. The low power graphical display is operated to visually present the status of the medical vaporizer. The medical vaporizer is disconnected from the external power source. The visual presentation of the status of the medical vaporizer is maintained on the low power graphical display in the absence of power from the external power source.

An exemplary embodiment of a vaporizer system includes a medical vaporizer and an anesthesia delivery machine. The medical vaporizer includes a liquid drug reservoir configured to receive and hold a liquid drug. The medical vaporizer further includes a low power graphical display configured to intermittently receive power. The low power graphical display is operable to visually present information and maintain the visual presentation of information in the absence of power. The medical vaporizer includes a controller that is configured to intermittently receive power. Upon receiving power, the controller operates to determine a status of the medical vaporizer and operates the low power graphical display to present the status of the medical vaporizer as visually presented information. The anesthesia delivery machine is configured to connect to the medical vaporizer. The anesthesia delivery machine is configured to supply power to the medical vaporizer when the anesthesia machine is connected to the medical vaporizer.

DETAILED DISCLOSURE

In the following detailed disclosure, reference is made to the accompanying drawings. From a part thereof, an image is shown by way of illustration of specific embodiments, which may be practiced. These embodiments are described in sufficient detail to enable those skilled in the art to practice the embodiments, and it is to be understood that other embodiments may be utilized and that logical, mechanical, electrical, and other changes may be made without departing from the scope of the embodiment. The following detailed description is, therefore, not to be taken in a limiting sense. It is to be understood that the exemplary embodiments depicted in the Figures and described herein, have been selected for the purposes of description and disclosure and certain embodiments may be implemented with additional features or only portions of the features as described herein while still remaining within the scope of the present disclosure as will be recognized by one of ordinary skill in the art.

Figure 1:
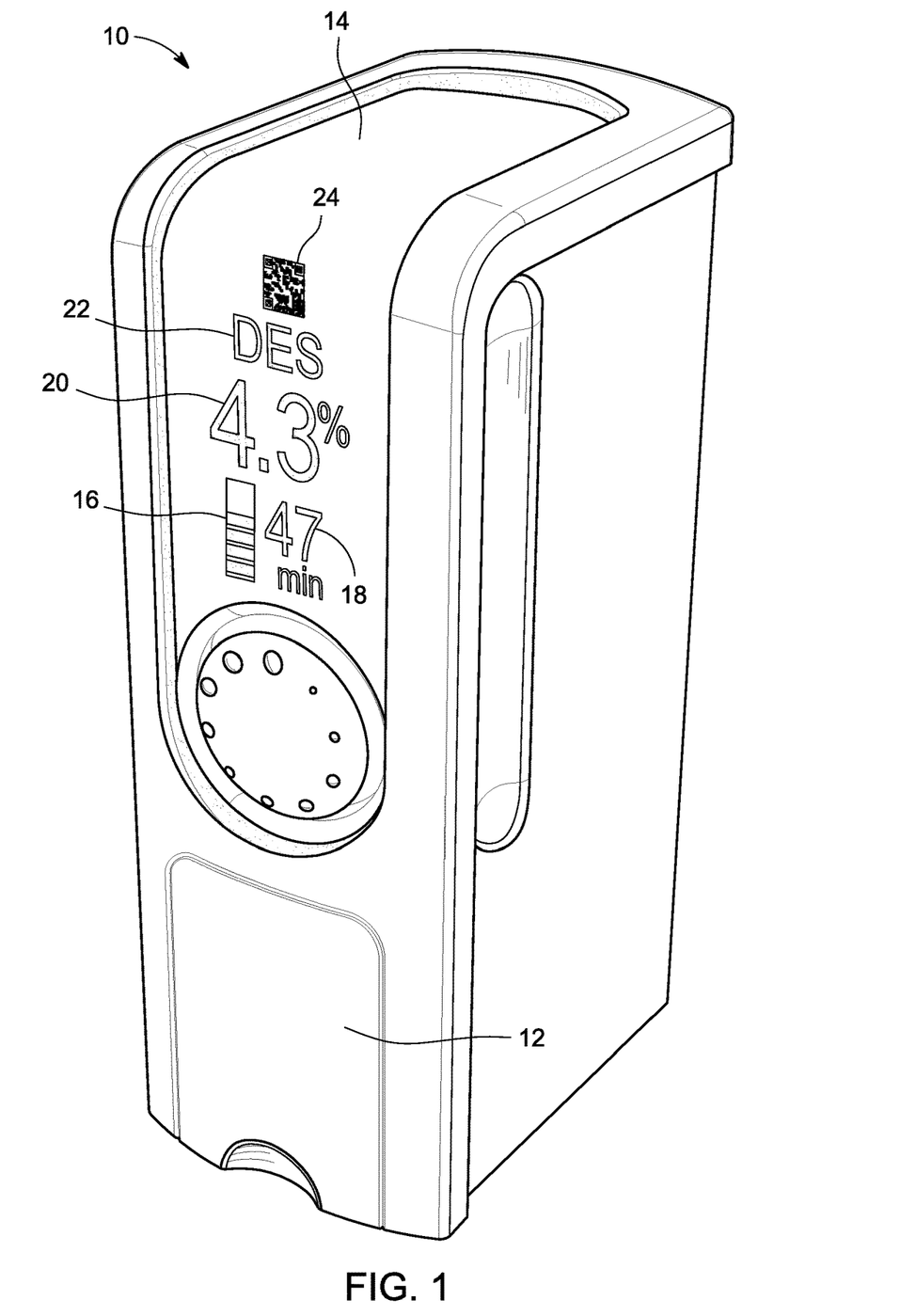
FIG. 1 depicts an exemplary embodiment of a medical vaporizer.

FIG. 1 depicts an exemplary embodiment of a medical vaporizer 10. The medical vaporizer 10 internally contains a liquid drug reservoir (not depicted), which may alternatively be known as a sump that is configured to receive and hold liquid drug, exemplarily an anesthetic agent. The medical vaporizer 10 includes a filling interface 12 which is configured to receive a source of the liquid drug, exemplarily a bottle (not depicted) and transfer the liquid drug from the liquid drug source to the liquid drug reservoir. The medical vaporizer operates, often in conjunction with an anesthesia delivery machine (not depicted), as described in further detail herein, to change the state of the liquid drug into a gaseous drug for delivery to the patient. When not actively in use, the vaporizer 10 may hold the liquid drug sealed within the liquid drug reservoir or otherwise within the vaporizer 10 such that no liquid or gaseous drug escapes from the medical vaporizer 10. The medical vaporizer 10 further includes a graphical display 14 which, as described in greater detail herein, is a low power graphical display. In embodiments, the low power graphical display 14 is implemented with an electronic ink graphical display. Electronic ink graphical displays may exemplarily be constructed as electrophoretic displays which form visual images by arranging charged pigment particles using an applied electric field. However, a person of ordinary skill in the art would recognize that there are other techniques and implementations to construct electronic ink displays or other low power graphical displays. In embodiments, the low power graphical display, exemplarily the electronic ink display, is capable of holding a static visual presentation of text and/or images without the further application of electricity.

As will be described in further detail herein, the low power graphical display 14 may be configured and operated to visually present a variety of information, including a status of the medical vaporizer 10. As exemplarily depicted in FIG. 1, the low power graphical display 14 presents a graphical indication of a remaining volume 16 of the liquid drug, a temporal indication 18 of the remaining liquid drug, a concentration of the liquid drug 20, and an identification of the liquid drug 22, exemplarily Desflurane. The low power graphical display 14 further visually presents a two-dimensional code 24, exemplarily a quick response (QR) code. However, it will recognized that in alterative embodiments other graphical forms of conveying data, including, but not limited to one-dimensional bar codes may be used.

Figure 2A:
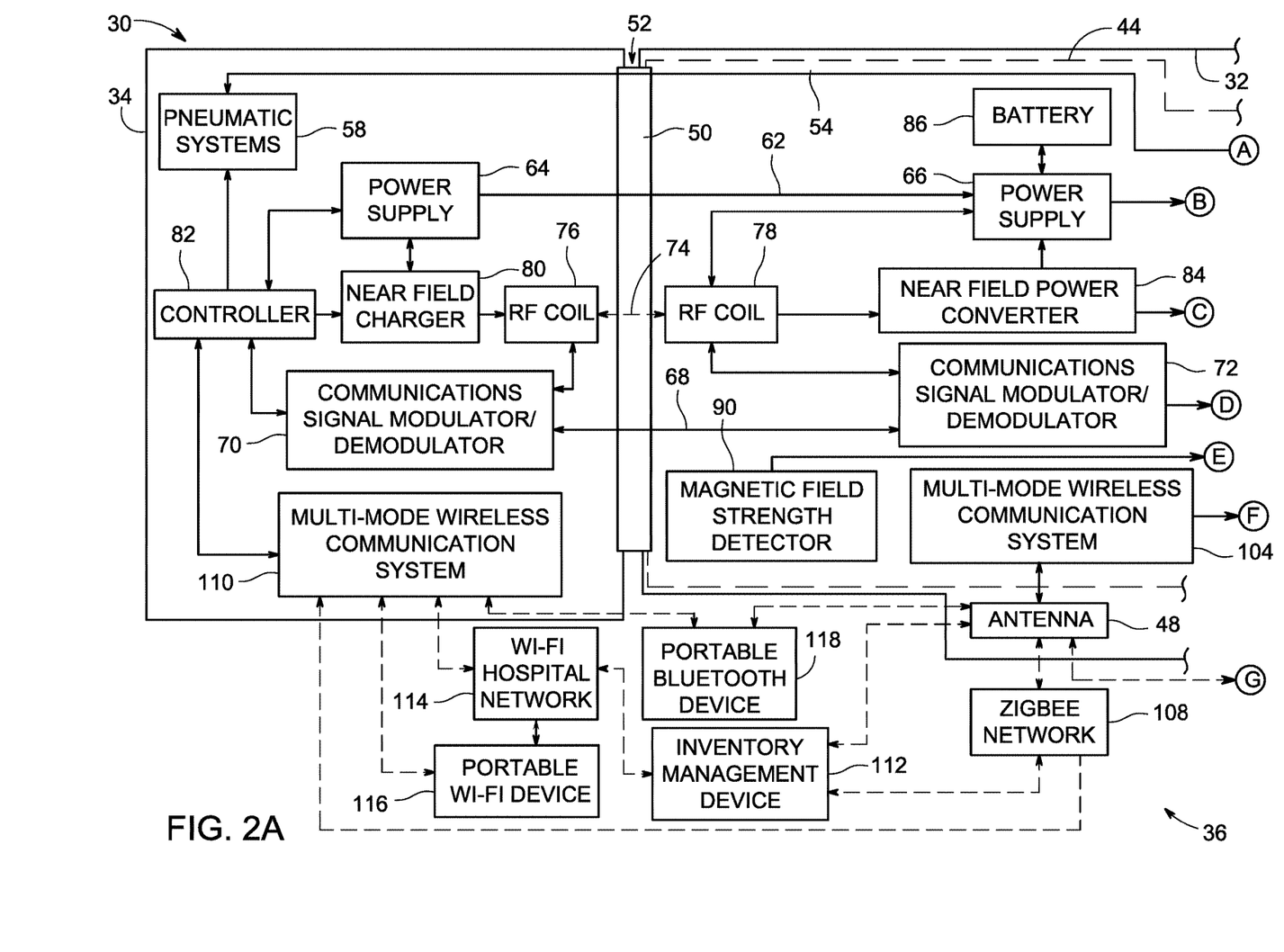
FIGS. 2A and 2B are a schematic diagram of an exemplary embodiment of a vaporizer system.
Figure 2B:
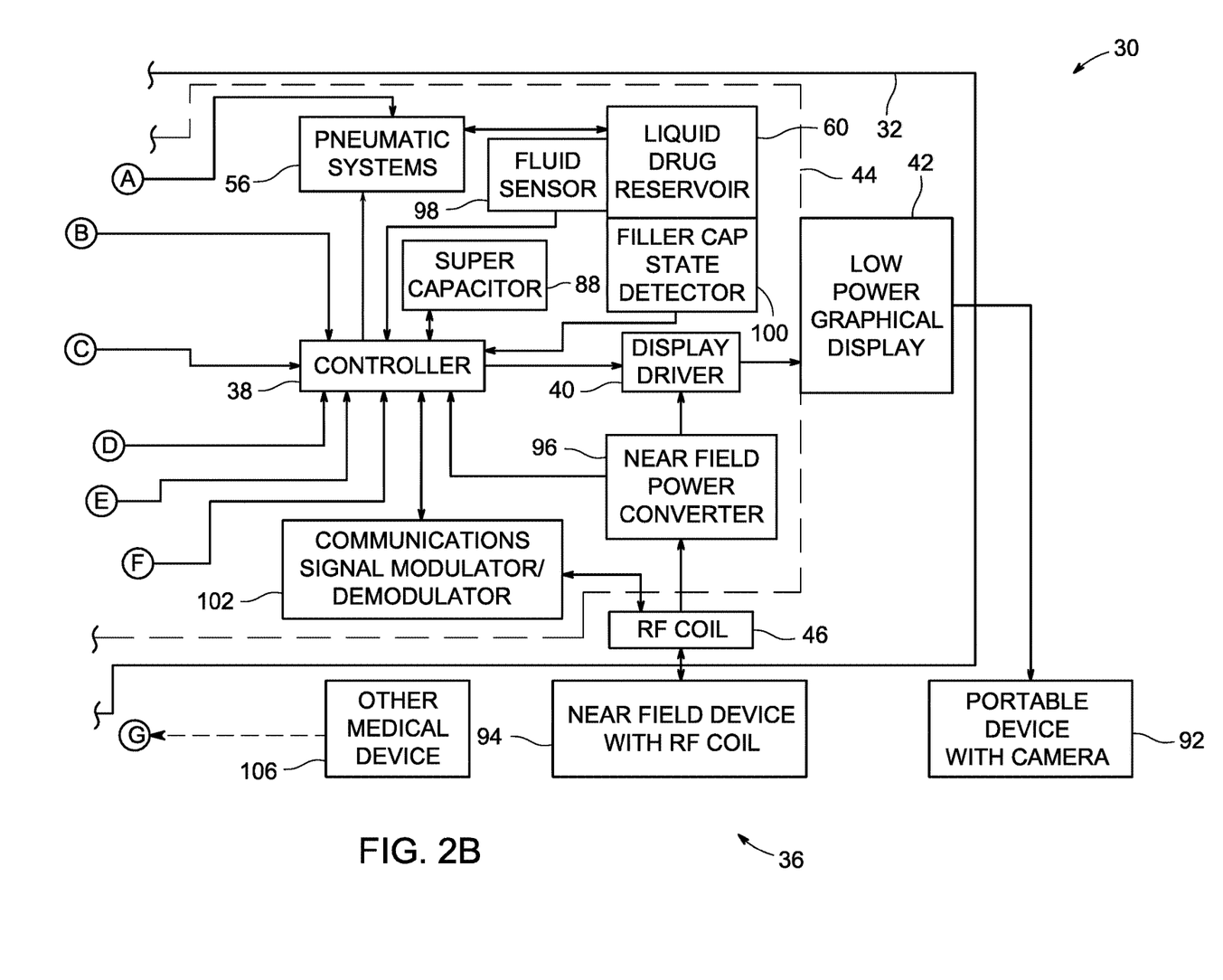

FIGS. 2A and 2B are a schematic diagram of an exemplary embodiment of a vaporizer system 30. In the exemplary embodiment of the vaporizer system 30 depicted in FIGS. 2A and 2B, the vaporizer system 30 generally includes a medical vaporizer 32, an anesthesia delivery machine 34, and at least one auxiliary communication device 36. It will be recognized that the exemplary embodiment of the vaporizer system 30 as depicted and described with respect to FIGS. 2A and 2B is merely exemplary of embodiments of vaporizer systems and alternative embodiments consistent with the present disclosure may incorporate additional components, or fewer components still remaining within the scope of the present disclosure.

The medical vaporizer 32 includes a controller 38 that exemplarily includes a computer readable medium (not depicted) that is programmed with computer readable code that upon execution of the computer readable code by the controller causes the controller to carry out the functions and operations as described in further detail herein. The controller 38 may also include memory in the form of a computer readable medium that stores a plurality of data fields for receiving and/or storing information as described in further detail herein. The controller 38 may operate, in conjunction with or in association with a display driver 40 to operate a low power graphical display 42. As previously described, the low power graphical display 42 may exemplarily be an electronic ink graphical display.

Embodiments of the medical vaporizer 32 may exemplary include electromagnetic shielding 44. Such electromagnetic shielding 44 may exemplarily shield the electronics and components contained therein from electromagnetic induced capacitances or electromagnetic induced inductances, exemplarily as may be caused by the electromagnetic field generated by a magnetic resonance imaging (MRI) device. It is to be noted that the low power graphical display 42 is located outside of the electromagnetic shielding 44. Also external to the electromagnetic shielding 44 is a radio frequency (RF) coil 46 and, in exemplary embodiments, an antenna 48. Embodiments implementing the RF coil 46 and/or antenna 48 will be described in further detail herein.

Embodiments of the medical vaporizer 32 further include an anesthesia machine connector 50 that exemplary bridges an interface 52 between the medical vaporizer 32 and the anesthesia delivery machine 34. In embodiments, the anesthesia machine connector 50 facilitates at least a physical connection between the medical vaporizer 32 and the anesthesia delivery machine 34 across the interface 52 such as to facilitate a pneumatic connection 54 between the pneumatic system 56 of the medical vaporizer and the pneumatic system 58 of the anesthesia delivery machine 34. As will be described in further detail herein, the pneumatic system 56 of the medical vaporizer 32 is connected to the liquid drug reservoir 60 and the pneumatic system 56 exemplarily converts the liquid drug to a gaseous state and the gaseous drug is transferred across the pneumatic connection 54 to the pneumatic system 58 of the anesthesia delivery machine 34 through which the gaseous drug can be delivered to the patient by the pneumatic system 58.

The medical vaporizer 32 is also wired and/or wirelessly connected to the anesthesia delivery machine 34 when the medical vaporizer 32 and anesthesia delivery machine 34 are connected across the interface 52. In an exemplary embodiment of a wired connection, a wired power connection 62 connects a power supply 64 of the anesthesia delivery machine 34 with a power supply 66 of the medical vaporizer 32. The wired power connection 62 facilitates the transfer of power from the power supply 64 to the power supply 66, such that the medical vaporizer 32 receives power and is powered when the medical vaporizer 32 is connected to the anesthesia delivery machine 34. In a wired connection embodiment, the vaporizer system 32 further includes a wired data connection 68 whereby communications data is transferred between a communication modulator/demodulator 70 of the anesthesia delivery machine 34 and a communication modulator/demodulator 72 of the medical vaporizer 32. The wired data connection 68 exemplarily facilitates the transfer of data, as disclosed in further detail herein and associated with particular exemplary embodiments.

In still further embodiments, the medical vaporizer 32 and anesthesia delivery machine 34 are connected by a wireless connection 74. The wireless connection 74 may exemplarily be between an RF coil 76 of the anesthesia delivery machine 34 and an RF coil 78 of the medial vaporizer 32. The anesthesia delivery machine 34 can include a near field charger 80 connected to the power supply 64 and operated by a controller 82 of the anesthesia delivery machine 34 to energize the RF coil 76 such that the wireless connection 74 enables the transfer of power through the RF coil 78 to a near field power converter 84 of the medical vaporizer 32 which can convert the energization received at the RF coil 78 into electrical power that may be directed to the power supply 66, or exemplarily to the controller 38 at other electrical components in the medical vaporizer 32, such that the medical vaporizer 32 may operate in a full power mode when wirelessly connected to the anesthesia delivery machine 34.

The communication modulator/demodulator 70 of the anesthesia delivery machine may exemplarily also be connected to the RF coil 76 such that the wireless connection 74 also transmits data between the anesthesia delivery machine 34 and the medical vaporizer 32 as described in further detail herein, in embodiments, the RF coil 78 of the medical vaporizer 32 is also connected to the communication modulator/demodulator 72 of the medical vaporizer in order to facilitate this transfer of communication data.

In an exemplary embodiment, the data connection between the medical vaporizer 32 and the anesthesia delivery machine 34 may exemplarily operate to transfer stored data and operational statuses between the two devices. In an embodiment, the medical vaporizer 32 may send an operational status, liquid drug amount, liquid drug identification, calibration table, or other information to the anesthesia delivery machine 34. The anesthesia delivery machine 34 may send an operational, service, or maintenance status of the anesthesia delivery machine 34 to the medical vaporizer 32 for storage as disclosed in greater detail herein.

In embodiments, the power supply 66 of the medical vaporizer 32 may operate to charge a battery 86 in order to store electrical power, although it will be understood that in alternative embodiments, no battery 86 is used. In alternative embodiments, a super capacitor 88 operates to store a charge which may be drawn upon for minimal operations in a low power operational mode of the medical vaporizer 32 when the medical vaporizer 32 is disconnected from an external power source, for example, the anesthesia delivery machine 34, as will be described in further detail herein. It will also be recognized that in still further embodiments, no energy storage component is used, other than those that may be an integral component of the controller or other electronics in the medical vaporizer.

Embodiments of the medical vaporizer 32 may further include a magnetic field strength detector 90, exemplarily located internal to the electromagnetic shielding 44. The magnetic field strength detector 90 may be communicatively connected to the controller 38 and serve as a functional indication as to the effectiveness of the shielding provided by the electromagnetic shielding 44.

As will be described in further detail herein with respect to particular embodiments, the vaporizer system 30 may include one or more auxiliary communication devices 36 which can communicate with the medical vaporizer 32 in the manners as described herein. In one embodiment, the auxiliary communication device 36 is a portable device 92 which either is or includes a camera. Such portable device 92 is exemplarily a cell phone or a tablet computer that includes an integral camera that is operable to capture an image of a QR code or other bar code presented on the low power graphical display and the portable device 92 is operable to interpret the data encoded in the QR code.

In another embodiment, the auxiliary communication device 36 is a near field device 94 that exemplarily includes an RF coil. The near field device 94 may operate in the manner as disclosed in further detail herein to interact with the RF coil 46 of the medical vaporizer 32, particularly when the medical vaporizer 32 is disconnected from the anesthesia delivery machine 34. Interaction between the RF coil of the near field device 94 and the RF coil 46 of the medical vaporizer 32 enables a near field power converter 96 to convert the electromagnetic energy received by the RF coil 46 into energization power suitable for use by electrical components of the medical vaporizer 32, exemplarily, the controller 38, the display driver 40, and the low power graphical display 42. In such embodiments as will be described in further detail herein, the medical vaporizer 32 can use the power obtained from the near field device 94 to operate in a low power mode such that the medical vaporizer 32 can update the status of the medical vapor and/or operate the low power graphical display 42 through the display driver 40 in order to update the presentation of information on the low power graphical display 42. In one non-limiting example, the medical vaporizer 32 may use the power from the near field power converter 96 to perform a reading by a fluid sensor 98 associated with the liquid drug reservoir 60 and provide this reading from the fluid sensor 98 to the controller 38. The controller 38 may then operate the low power graphical display 42 through the display driver 40 to update the presentation of the amount of liquid drug in the liquid drug reservoir 60.

In an alternative embodiment, the super capacitor 88 may provide sufficient power to the medical vaporizer 32 when the medical vaporizer 32 is disconnected from the anesthesia delivery machine 34 such that a filler cap state detector 100 may operate in conjunction with the liquid drug reservoir 60 such as to detect when the liquid drug reservoir 60 is accessed such as in a filling procedure. Upon detecting that the filler cap has been opened and/or closed, a reading of the volume of liquid drug in the liquid drug reservoir 60 by the fluid sensor 98 may be performed and the controller 38 uses this information to update the low power graphical display 42 to reflect the refilled volume of the liquid drug. This feature may be useful in embodiments wherein the medical vaporizers 32 are stored apart from anesthesia delivery machines 34 and may be periodically refilled while in storage such that the medical vaporizers 32 are ready for subsequent use.

Referring back to the RF coil 46 and the near field device 94, in still further exemplary embodiments, the near field device 94 may also communicatively connect to the medical vaporizer 32 through the RF coil 46. Such communication data may be directed through a communications signal modulator/demodulator 102. The communication signal modulator/demodulator 102 may exemplarily facilitate communication between the controller 38 of the medical vaporizer 32 and the near field device 94, through the RF coil 46. In still further embodiments as will be described in more detail herein, when the medical vaporizer 32 receives power from the near field device 94 as provided by the near field power converter 96, the controller 38 may achieve communications or data transfer with the near field device 94 and in such embodiments the determined updated status of the medical vaporizer 32 may be transmitted to the near field device 94 with or without updating the low power graphical display 42. In still further embodiments, any of a variety of stored or monitored static or dynamic information, as disclosed in greater detail herein, may be transmitted from the controller 38 to the near field device 94, when a communication and power connection have been established between the near field device 94 and the RF coil 46 of the medical vaporizer 32.

As previously described, the medical vaporizer 32 may also include an antenna 48, exemplarily an RF antenna; however, it will be recognized that other forms of wireless communication devices, including but not limited to optical communication devices, may be used. The antenna 48 is connected to a multi-mode wireless communication system 104 that operates when the medical vaporizer 32 has sufficient power to facilitate the transfer of data from the medical vaporizer 32. This may be the medical vaporizer 32 is connected to the anesthesia delivery machine 34, an external charging station (wired or wireless charging), or the medical vaporizer 32 has sufficient stored energy exemplarily in a battery or super capacitor.

Any of a variety of other auxiliary communication devices 36 that may be configured to connect to the antenna 48, these may include other medical devices 106 including, but not limited to patient monitoring devices, or patient medical records and tracking systems. In still further embodiments, a Zig Bee network 108 may be established in a medical care setting. Zig Bee is a communication protocol specification used to create personal area networks. Zig Bee is a low-cost and low-power standard for creating wireless networks between small, low-power digital radios. Such a meshed Zig Bee network 108 may be used to exemplarily establish a data communication with a multi-mode wireless communication system 110 of the anesthesia delivery machine 34 or to connect to any of a variety of other portable wireless devices, including an inventory management device 112. Such an inventory management device 112 may be used in a setting as previously described, wherein a plurality of medical vaporizers 32 are stored at a single location and filled with liquid drug such that the medical vaporizers 32 are ready to be used with anesthesia delivery machines. An inventory management device 112 may wirelessly connect to each of the medical vaporizers 32, exemplarily directly to the antenna 48, or through the exemplarily mentions Zig Bee network 108 such as to receive the current status and other information as may be broadcasted by the medical vaporizer 32, such as to identify the medical vaporizer 32 in the hospital inventory, and to update a status thereof. The inventory management device 112 may further also connect to a broader hospital network 114, such as a Wi-Fi network 114. The hospital Wi-Fi network 114 may facilitate the transfer of information collected by the inventory management device 112 and may also communicatively connect back to a multi-mode wireless communication system 110 of the anesthesia delivery machine 34 or to other portable Wi-Fi devices 116. In still further embodiments, the antenna 48 of the medical vaporizer 32 may also be operable to communicatively connect to a portable device 118 exemplarily on the Bluetooth wireless technology standard.

Figure 3:
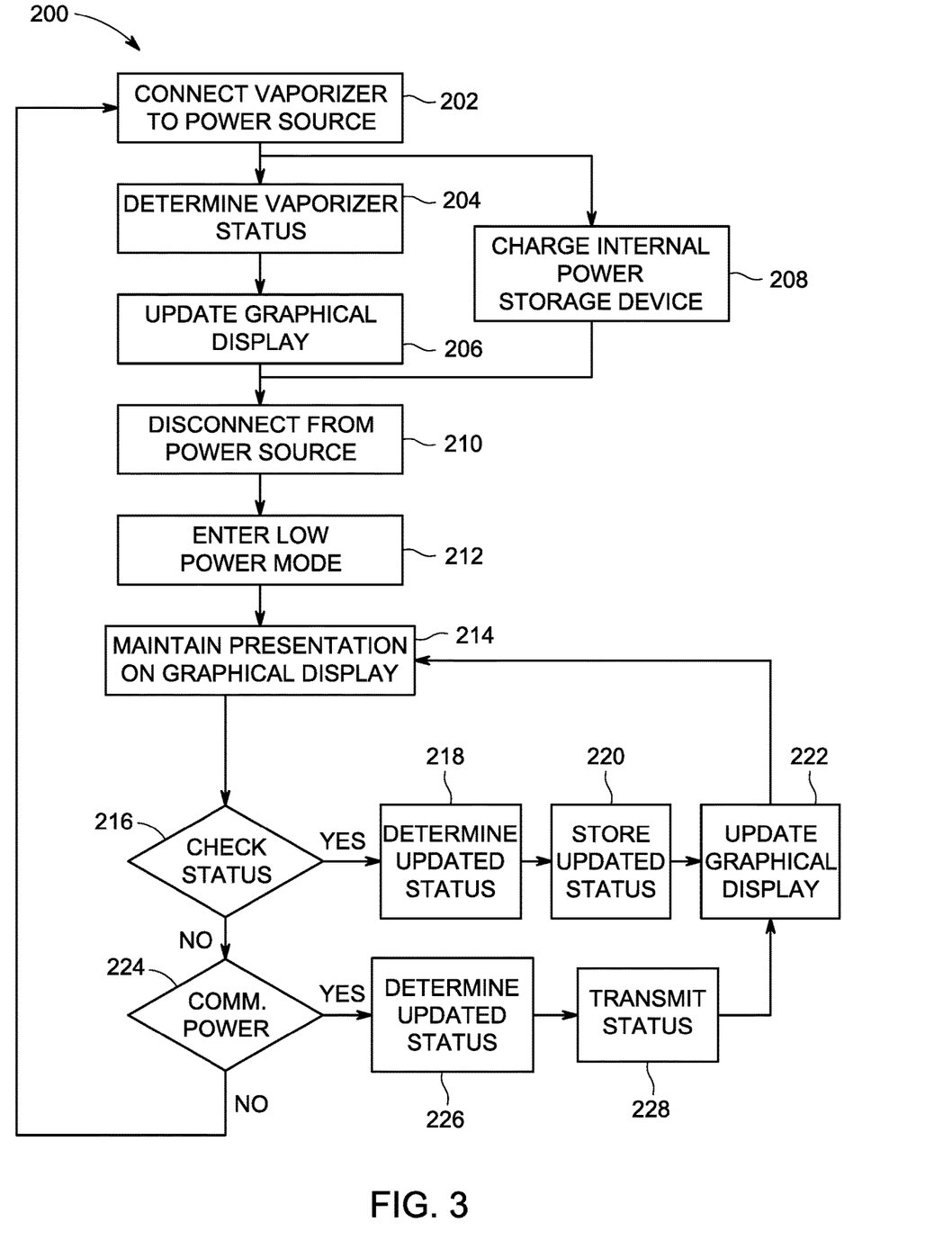
FIG. 3 is a flow chart of an exemplary embodiment of a method of operation of a medical vaporizer.

FIG. 3 is a flow chart that depicts an exemplary embodiment of a method 200 of operation of a medical vaporizer. The description herein of the method 200 is understood to be exemplary in nature and a person of ordinary skill in the art will recognize that alternative embodiments of the method as described herein may be implemented with more or fewer steps or the steps may be performed in an alternative order while maintaining the functionality of the systems and methods as described herein. A person of ordinary skill in the art will also recognize that additional features, operations, functions, and interactions occurring within embodiments of the vaporizer system 30, which may carry out embodiments of the method 200, will be described herein with respect to the method 200.

Referring now to FIGS. 1-3, the method 200 begins with the connection of the vaporizer to a power source at 202. The power source to which the vaporizer is connected is an external power source and is exemplarily an anesthesia delivery machine as described above. It will also be recognized that in alternative embodiments, the external power source may be a charging station or other charging device that may exemplarily provide power to the vaporizer by wired or wireless transmission implementations.

While receiving power from the external power source at 202 the vaporizer operates at 204 to determine a vaporizer status. As described above, the determined status of the medical vaporizer may exemplarily be a fill level of liquid drug in the liquid drug reservoir or other dynamic information. It will be recognized that the determined vaporizer status may be one or more of any of a variety of information. In exemplary embodiments, the information that may be monitored and/or presented by the medical vaporizer may be static information or dynamic information. It will be recognized that in an exemplary embodiment, static information may be programmed into the medical vaporizer as part of manufacture of the medical vaporizer or such static information may be updated or entered by a user input control. On the other hand, dynamic information may be information that changes and may be monitored, determined, or received by the medical vaporizer and thus stored, presented, or transmitted as disclosed herein.

Exemplary types of static information may include an identification of the liquid drug type, a device serial number, a manufacturer identification, a manufacturing date, a calibration table, or a website with additional information; however, it will be recognized by a person of ordinary skill in the art that this list is non-limiting and that other forms of static information may be used in embodiments as disclosed herein. Dynamic information may include, in addition to a fill level of liquid drug, a last service date of the medical vaporizer, an operation log of the medical vaporizer, a current location or a location log of determined locations of the medical vaporizer, a drug level history, or a date of a most recent fill of liquid drug; however, a person of ordinary skill in the art will recognize that other forms of dynamic information may also be determined, monitored, or received. In still further embodiments, the dynamic information may be received by the medical vaporizer and such dynamic information may exemplarily include information regarding an anesthesia delivery machine to which the medical vaporizer is or was connected, such information may include specific information regarding anesthesia machine status or state, including an on/off state, concentration setting, maintenance and/or service information, and/or operational statuses. This dynamic information may also exemplarily include a log of multiple statuses and/or states of an anesthesia delivery machine. In a still further embodiment, the medical vaporizer may maintain a log of specific anesthesia delivery machines to which the medical vaporizer has been connected and dates, times, and operational information regarding each of these connections.

Referring back to FIG. 3, at 206, the graphical display is updated, exemplarily by the controller and display driver of the medical vaporizer to present the determined vaporizer status on the low power graphical display of the medical vaporizer. In an exemplary embodiment, the low power graphical display of the medical vaporizer may also be operated at 206 to present additional dynamic or static information as described above. In one exemplary embodiment, at least a portion of the information, which may include static and/or dynamic information, is presented in the low power graphical display as one or more two-dimensional matrix codes or other bar codes, which in exemplary embodiments, is a quick response (QR) code.

Figure 4:
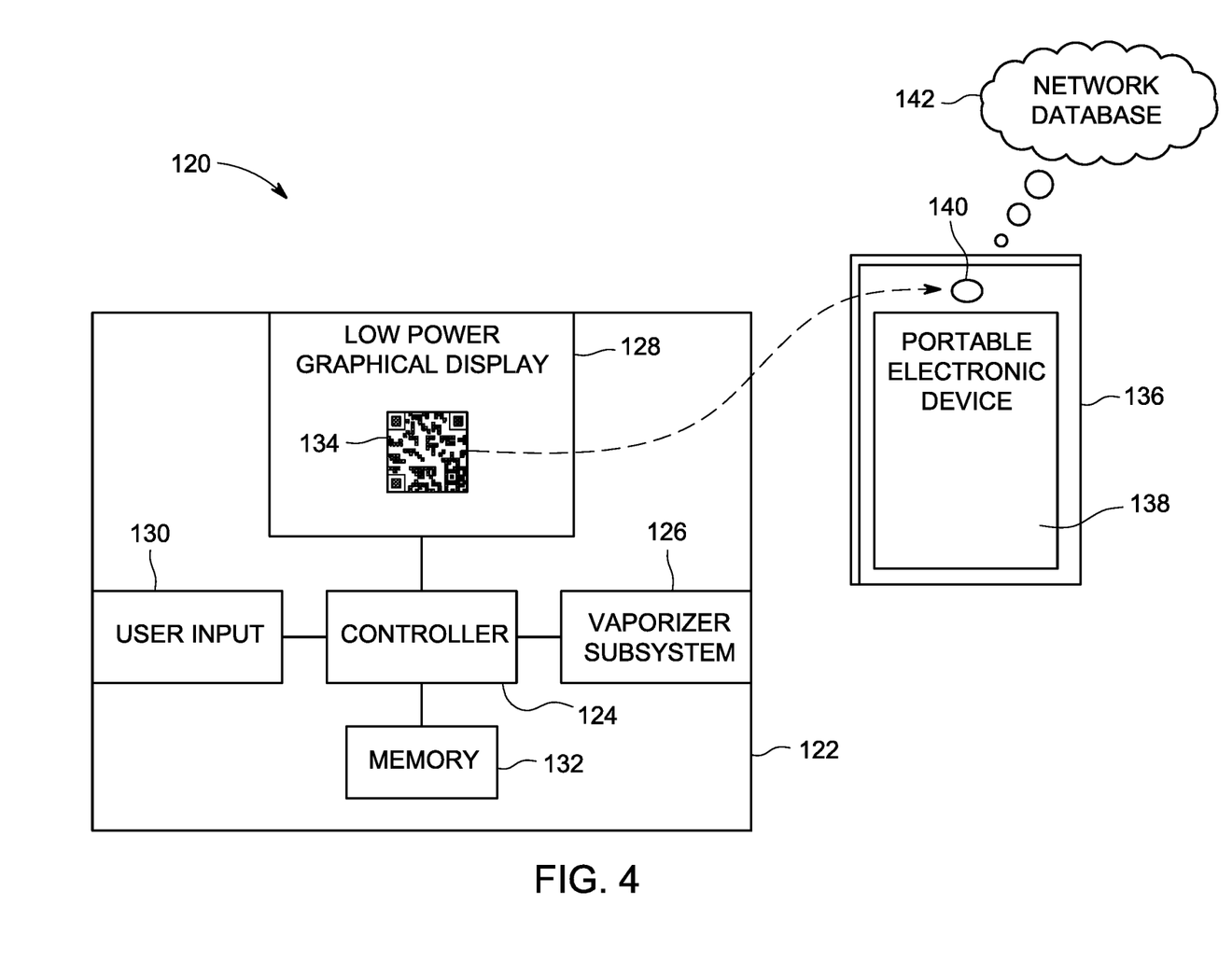
FIG. 4 is a block diagram of an alternative exemplary embodiment of a vaporizer system.
Figure 5:
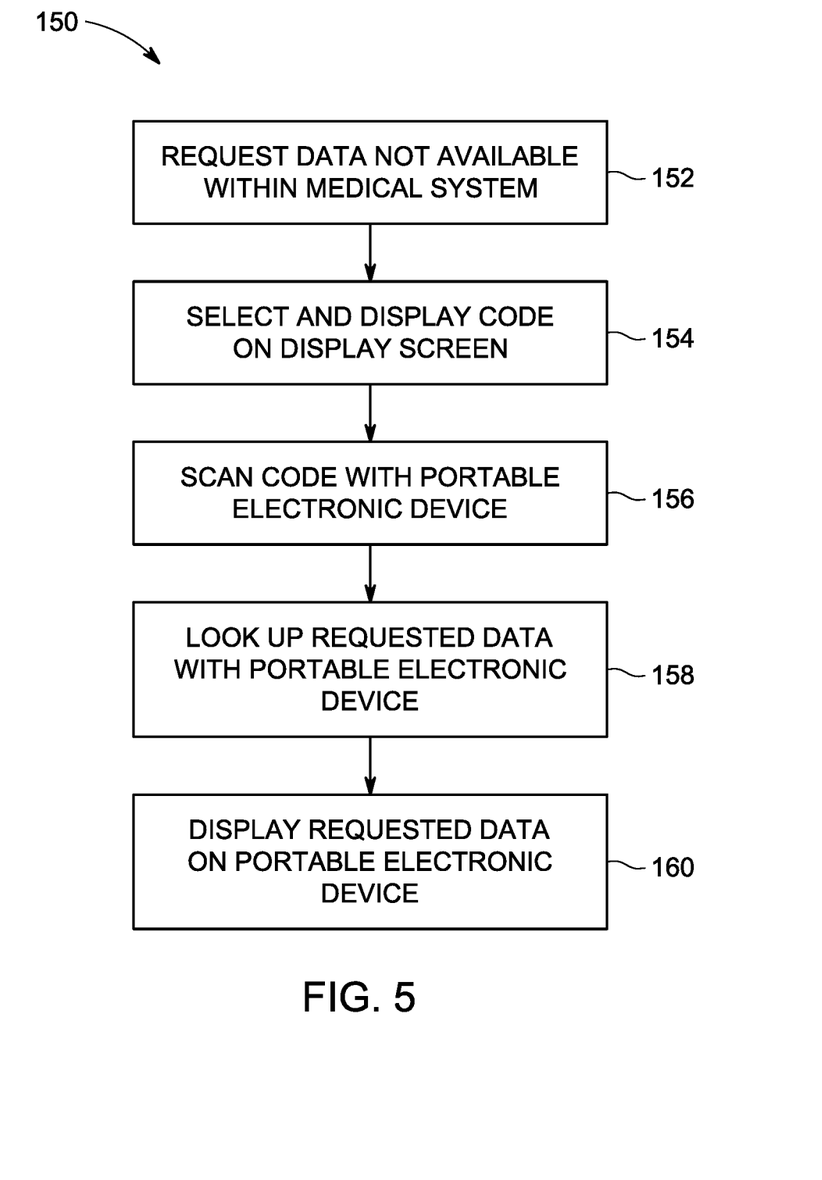
FIG. 5 is a flow chart of an alternative exemplary embodiment of a method of operation of a medical vaporizer.

Additional information regarding embodiments that use an exemplary QR code to present information on the low power graphical display will be described in further detail herein with respect to FIGS. 4 and 5. FIG. 4 is a block diagram of an exemplary embodiment of a vaporizer system 120 that presents information, at least in part, using a two-dimensional code. FIG. 5 is a flow chart of an exemplary embodiment of a method 150 of operation of a medical vaporizer.

FIG. 4 is an additional exemplary embodiment of a vaporizer system 120. The vaporizer system 120 includes a medical vaporizer 122 which includes a controller 124, a vaporizer subsystem 126, a low power graphical display 128, a user input 130, and a non-transient computer-readable memory 132. The controller 124 includes a processor, such as a programmable microprocessor. The controller 124 is in communication with the vaporizer subsystem 126, the user input 130, the low power graphical display 128, and the memory 132. It will be recognized that similar components have been described above and specific features as described above may be incorporated into embodiments of the vaporizer system 120.

Exemplarily, the medical vaporizer 122 may include features of embodiments of the medical vaporizer as described above with respect to FIGS. 1-3. The vaporizer subsystem 126 may exemplarily include these features of the vaporizer 10 of FIG. 1 or vaporizer 32 of FIG. 2 not otherwise depicted in FIG. 4. The vaporizer subsystem 126 is in two-way communication with the controller 124, such that control signals may be communicated from the controller to the vaporizer subsystem 126, and data collected by the vaporizer subsystem 126 may be returned to the controller 124 for processing and display on the low power graphical display 128. The data collected by the vaporizer subsystem 126 may include dynamic information as described above. The user input 130 may be, for example, a keyboard, mouse, trackball, touch pad or other known input device. In some embodiments, the user input 130 may be a communicatively connected device external to the vaporizer 122. In an embodiment, the user input device 130 facilitates the entry of static or dynamic information as described above.

The memory 132 stores a plurality of signal processing, display, and communication algorithms for execution by the controller. In exemplary embodiments the memory 132 also defines a plurality of data fields for receiving, for example, static or dynamic information. The memory 132 may additionally store a plurality of optically machine-readable codes which may be selectably or automatically displayed on the low power graphical display 128. As illustrated in FIG. 4, an optically machine-readable code 134 may take the form of a two-dimensional code, such as a QR-code 134. In other embodiments, the optically machine readable code may be another type of two-dimensional code. In still other embodiments, the optically machine readable code may be a one-dimensional code, such as a barcode. As described in further detail herein, the controller 124 may operate the low power graphical display 128 to visually present at least some of the information, which may include static or dynamic information in the form of the optically machine-readable code 134.

With continued reference to FIG. 4, the vaporizer system 120 may be used in conjunction with a portable electronic device 136. The portable electronic device 136 may be, for example, a smartphone such as an Apple iPhone and equivalents thereof, or a tablet computer such an Apple iPad and equivalents thereof. The portable electronic device 136 includes a display 138, such as a touchscreen display, and a camera 140. With appropriate application software, as known in the art of portable electronic devices, the camera 140 can function as an optical scanner for reading an optically machine readable code (e.g., the optically machine readable code 134 of the medical vaporizer 122). The portable electronic device 136 is in wireless communication with a network database 142, such as the Internet or a specialized network. The wireless connection may take the form of a wireless local area network (WLAN), such as a Wi-Fi connection, or a wireless telecommunication network (e.g., a 3G or 4G telecommunications network). In an exemplary embodiment, the portable electronic device 136 is the portable electronic device 92 of FIG. 2.

Referring to FIGS. 4 and 5, the controller 124 operates to present at least a portion of the static and/or dynamic information of the low power graphical display 128 as an optically machine readable code 134. In another embodiment, the controller, at 152, receives a request for data that is not available at the medical vaporizer 122. In an embodiment, the displayed code 134 is selected at 154 from a library of possible codes stored on the memory 132. In embodiments this selected code is representative of at least a portion of the static and/or dynamic information or the requested data not available at the vaporizer.

With the machine readable code 134 displayed on the low power graphical display 128 of the medical vaporizer 122, the user, at 156, scans the machine readable code 134 with the camera 140 (i.e., scanner) of the portable electronic device 136. The portable electronic device 136 identifies the machine readable code 134 and responds by looking up the encoded information at 158. Depending on the encoded information, the requested information may be found internally on the portable electronic device, or it may be accessed from the external network database. The portable electronic device may also forward an email, SMS, or other messages to a support center with the data needed to provide customer support. In still further embodiments, the machine readable code may embody a request for information to be entered into the medical vaporizer 122, exemplarily static information.

Once the information is identified and received by the portable electronic device 136, the graphical display 138 is operated by the portable electronic device 136 to visually present the static and/or dynamic information or requested data at 160. If, for example, the user has requested technical support, or "help" assistance, then technical support information or instructions will appear on the display 138 of the portable electronic device 136, in order to guide the user to a solution. In another example, the user may request an ideal or comparative reference image to display on the portable electronic device, for comparison to image data displayed on the display screen of the medical system. In another example, the user may request live support from another medical professional. In still further embodiments, the optically machine readable code may encode dynamic information, for example, a current fill level of liquid drug in the medical vaporizer 122, or static information, for example a manufacturer or a serial number of the medical vaporizer 122. The graphical display 138 may operate to present this information.

In some embodiments, the machine readable code 134 may be displayed automatically in response to the controller detecting a pre-defined condition. Examples of pre-defined conditions may include a fault with the vaporizer subsystem 126, or a data field that is required to be filled prior to completion of a process or algorithm. In another specific embodiment, the machine readable code may also continually represent a status of the vaporizer subsystem 126.

In some embodiments, the machine readable code 134 may include data, including the static or dynamic information, to be uploaded to an external database. In these embodiments, the machine readable code 134 includes embedded data, rather than merely being a request for data. The data is then uploaded to the portable electronic device 136 by scanning the optically machine readable code 134 with the camera 140. The data embedded in the optically machine readable code 134 may then be uploaded to the network database 142 from the portable electronic device 136 for further analysis or storage.

In some embodiments, the machine readable codes 134 as described herein may include embedded security credentials that provide for authentication between the medical vaporizer 122 and the portable electronic device 136. In these embodiments, only medical vaporizers and portable electronic devices 136 configured to receive and authenticate the security credentials may be used with one another. Such security credentials provide additional security advantages when dealing, for example, with confidential patient health information.

Referring back to the flow chart of FIG. 3 and the exemplary embodiments depicted in FIGS. 1 and 2, while the medical vaporizer is connected to the external power source, and concurrently with the determined vaporizer status and the operation of the graphical display as previously described, in embodiments of the medical vaporizer that include an internal power storage device, this internal power storage device is charged at 208. As previously described, this internal power storage device may be a battery, but may also, in alternative embodiments, be a super capacitor. It is to be recognized that in embodiments of the method 200, the step of charging the internal power storage device at 208 may be optional, and in some embodiments, the medical vaporizer may not include an internal power storage device apart from those as may be integral components of the electronics found in the medical vaporizer.

At 210, the medical vaporizer is disconnected from the external power source. In embodiments, this disconnection may be the disconnection of the medical vaporizer from the anesthesia delivery machine. Upon disconnection of the medical vaporizer from the power source at 210, the medical vaporizer enters a low power mode at 212, which may be a low power configuration or low power operational state. In the low power mode, the medical vaporizer maintains presentation of the information on the graphical display at 214. In embodiments as described above, the graphical display is a low power graphical display, and may exemplarily be implemented as an electronic ink graphical display wherein the information visually presented on the graphical display is retained on the graphical display in the absence of further electrical power and persists until the graphical display further receives power and is actively updated.

Further in the low power mode, the medical vaporizer may determine if a status check is required at 216. In an exemplary embodiment, wherein the medical vaporizer includes an internal power storage device that has been charged by the external power source, the medical vaporizer may retain sufficient stored power such as to perform a minimal functionality low power status check, exemplarily to check a fill level of liquid drug in the liquid drug reservoir. In another exemplary embodiment, the medical vaporizer includes a filler cap state detector and the medical vaporizer only updates the fluid level if the filler cap state has changed. In an exemplary embodiment, the status checks may occur at regular intervals, or may occur upon the detection of another event, exemplarily a change in filler cap state. In still further embodiments, the determined medical vaporizer status may be a location of the medical vaporizer, which may be determined using any of a variety of location determination implementations, including, but not limited to GPS or wireless triangulation.

After the updated status is determined at 218, the updated status may be stored at 220. The updated status may be stored within a computer readable medium in the controller or integral with the controller or may be stored in a computer readable medium communicatively connected to the controller. The stored system may be later transferred or used to update the low power graphical display as disclosed herein. Exemplarily, the medical vaporizer may store the updated status until the medical vaporizer is receiving external power at which point the medical vaporizer may operate the low power graphical display or to transmit the updated status to another medical device.

In a further exemplary embodiment, the low power graphical display may be updated at 222 to reflect the detected updated status. In a non-limiting embodiment wherein the updated status is a volume of liquid drug in the liquid drug reservoir, the low power graphical display may be updated to reflect the detected drug level. In such embodiments, the internal power storage device, exemplarily a battery or super capacitor, stores a sufficient amount of power such that the medical vaporizer can determine such updated status and update the visual presentation on the low power graphical display.

Additionally, at 224, the medical vaporizer, while disconnected from the external power source, exemplarily the anesthesia delivery machine, may become communicatively connected with an auxiliary communication device which is exemplarily a near field communication device that includes an RF coil. Such an RF coil may transfer RF energization to the medical vaporizer which the medical vaporizer may convert into a sufficient amount of electrical power in order to determine the updated status of the medical vaporizer at 226. Such updated status determination at 226 may be similar as described above with respect to 218. In other embodiments, the detected updated status at 226 may differ from that at 218 in that the determined updates status at 226 may be performed in embodiments that do not include an internal power storage device or may incorporate a wider variety of determined updated statuses which may include other forms of dynamic information as described above, as the medical vaporizer has access to a power source, rather than drawing upon a reserved power supply.

In embodiments, as the communicative power source at 224 is a part of a communicative connection between the auxiliary communication device and the medical vaporizer, the medical vaporizer may operate to transmit the determined updated status at 228 to the auxiliary communication device. Additionally, the medical vaporizer may further operate to transmit any other static or dynamic information that the medical vaporizer may have stored within the communication abilities of the data connection and the auxiliary communication device. Additionally, the power provided to the medical vaporizer through the RF coil of the near field communication device may be sufficient in order to operate and update the visual presentation of information on the low power graphical display 222. It is understood that the medical vaporizer may operate in this manner until the medical vaporizer is connected again to an external power source, such as an anesthesia delivery machine, at 202.

In exemplary embodiments, a medical vaporizer is provided that is compatible with use in magnetic resonance imaging environments as the low power graphical display may be configured in a manner such that its operation is not interfered with by the strong magnetic fields created by the MRI device or such that the un-shielded components of the medical vaporizer (e.g. the low power graphical display) adversely interfere with the operation of the MRI device.

Additionally, embodiments of the medical vaporizer as disclosed herein have the further advantage of having an updateable graphical display that visually presents information regarding the status of the medical vaporizer, but that such visual presentation of the status of the medical vaporizer persists in the absence of an external power source. Still further embodiments of the medical vaporizer as disclosed herein achieve such status display functionalities further without an internal power storage device and only update such graphical display or medical vaporizer status when in connection with a source of power.

In embodiments of the low power graphical display, such low power graphical display may be implemented with one or more colored layers or filters, such that the low power graphical display is able to visually present information to include color coded designations or use color to highlight presented status information, exemplarily alerts. Non-limiting example of alerts that may be presented by the low power graphical display may be an alert for a low volume of liquid drug or an alert due to a maintenance or service status determination.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical vaporizer, comprising:
   a liquid drug reservoir configured to receive and hold a liquid drug;
   a low power graphical display configured to intermittently receive power, the low power graphical display operable to visually present information and maintain the visual presentation of information in the absence of power;
   a controller configured to intermittently receive power and upon receiving power, the controller operates to determine a level of the liquid drug in the liquid drug reservoir and operates the low power graphical display to present the level of the liquid drug in the liquid drug reservoir as visually presented information and wherein in the absence of external power to the medical vaporizer, the low power graphical display operates to maintain the visual presentation of the status of the level of the liquid drug in the liquid drug reservoir;
   an energy storage device connected to the controller and configured to receive external power from an external power source, wherein external power charges the energy storage device, and the controller receives power from the energy storage device in the absence of external power from the external source; and
   a filler cap state detector operably connected to the liquid drug reservoir, the filler cap state detector operable under power from the energy storage device to detect if the liquid drug reservoir is accessed while the medical vaporizer is in the absence of external power, wherein upon the controller receiving power, the controller operates to determine the level of the liquid drug in the liquid drug reservoir if the filler cap state detector indicates the liquid drug reservoir has been accessed while the medical vaporizer is in the absence of power.

2. A medical vaporizer, comprising:
   a liquid drug reservoir configured to receive and hold a liquid drug;
   a low power graphical display configured to intermittently receive power, the low power graphical display operable to visually present information and maintain the visual presentation of information in the absence of power;
   a controller configured to intermittently receive power and upon receiving power, the controller operates to determine a status of the medical vaporizer, wherein the status of the medical vaporizer comprises a level of the liquid drug in the liquid drug reservoir, and operates the low power graphical display to present the status of the medical vaporizer as visually presented information, wherein the controller operates the graphical display to present at least a portion of the visually presented information as a two-dimensional matrix code.

3. The medical vaporizer of claim 2, wherein the visually presented information comprises at least one of: a liquid drug type, a vaporizer serial number, a vaporizer manufacturer, a vaporizer manufacture date, a calibration table, a manufacturer website, a last service date, a maintenance log, an operation log, a current vaporizer location, a location log, liquid drug volume history, a date of fill, and a fill log, a maintenance alert, a service alert, and a current liquid volume alert.

4. The medical vaporizer of claim 2, wherein the low power graphical display is an electronic ink display.

5. The medical vaporizer of claim 2, wherein the medical vaporizer is compatible for use with a magnetic resonance imaging (MRI) machine.

6. The medical vaporizer of claim 2, wherein in the absence of external power to the medical vaporizer, the low power graphical display operates to maintain the visual presentation of the status of the medical vaporizer.

7. The medical vaporizer of claim 6, further comprising:
   an energy storage device connected to the controller and configured to receive external power from an external power source, wherein external power charges the energy storage device, and the controller receives power from the energy storage device in the absence of external power from the external source.

8. The medical vaporizer of claim 7, further comprising:
   a computer readable medium communicatively connected to the controller;
   wherein when the controller receives power from the energy storage device, the controller operates to intermittently update the determined status of the medical vaporizer and store the updated determined status in the computer readable medium.

9. The medical vaporizer of claim 8, wherein when the controller receives power from the power supply, the controller operates in a full power operational mode wherein the controller is operable to receive at least one user input and operates to modify the visually presented information on the low power graphical display according to the at least one user input.

10. A vaporizer system comprising:
    a medical vaporizer comprising:
    a liquid drug reservoir configured to receive and hold a liquid drug;
    a low power graphical display configured to intermittently receive power, the low power graphical display operable to visually present information and maintain the visual presentation of information in the absence of power; and a controller configured to intermittently receive power and upon receiving power, the controller operates to determine a status of the medical vaporizer and operates the low power graphical display to present the status of the medical vaporizer as visually presented information;

an anesthesia delivery machine configured to connect to the medical vaporizer, and configured to supply power to the medical vaporizer when the anesthesia delivery machine is connected to the medical vaporizer; and an inventory management device communicatively connected to at least one of the medical vaporizer and the anesthesia delivery machine, wherein the inventory management device receives the status of the medical vaporizer through communication with at least one of the medical vaporizer and the anesthesia delivery machine and the inventory management device operates to store the received status of the medical vaporizer;

wherein the anesthesia delivery machine is further configured to communicate anesthesia delivery machine data to the controller when the anesthesia delivery machine is connected to the medical vaporizer;

wherein the medical vaporizer comprises a computer readable medium upon which the controller stores the anesthesia delivery machine data; and wherein, upon receiving power, the controller of the medical vaporizer operates the low power graphical display to present the anesthesia delivery machine data.

11. The vaporizer system of claim 10, wherein the anesthesia delivery machine data comprises at least one of: anesthesia delivery machine status or state, anesthesia delivery machine concentration setting, anesthesia delivery machine maintenance or service information, an anesthesia delivery machine status log, or a log of anesthesia delivery machines to which the medical vaporizer has been connected.

12. The medical vaporizer of claim 10, wherein the low power graphical display is an electronic ink display.

13. The medical vaporizer of claim 10, wherein the medical vaporizer is compatible for use with a magnetic resonance imaging (MRI) machine.

14. The medical vaporizer of claim 10, wherein in the absence of external power to the medical vaporizer, the low power graphical display operates to maintain the visual presentation of the status of the medical vaporizer.

15. The medical vaporizer of claim 14, further comprising:

an energy storage device connected to the controller and configured to receive external power from an external power source, wherein external power charges the energy storage device, and the controller receives power from the energy storage device in the absence of external power from the external source.

16. The medical vaporizer of claim 15, further comprising:

a computer readable medium communicatively connected to the controller;

wherein when the controller receives power from the energy storage device, the controller operates to intermittently update the determined status of the medical vaporizer and store the updated determined status in the computer readable medium.

* * * * *